| United States Patent [19] | [11] | 4,022,913 |
|---|---|---|
| Newmark | [45] | May 10, 1977 |

[54] HIGH POTENCY VITAMIN A COMPOSITIONS

[75] Inventor: Harold Leon Newmark, Maplewood, N.J.

[73] Assignee: Hoffmann-La Roche Inc., Nutley, N.J.

[22] Filed: July 3, 1975

[21] Appl. No.: 593,149

Related U.S. Application Data

[63] Continuation of Ser. No. 397,192, Sept. 13, 1973, abandoned, which is a continuation of Ser. No. 111,120, Jan. 11, 1971, abandoned, which is a continuation-in-part of Ser. No. 816,106, April 14, 1969, abandoned.

[52] U.S. Cl. .............................................. 424/344
[51] Int. Cl.² ........................................ A61K 31/07
[58] Field of Search ..................................... 424/344

[56] References Cited

UNITED STATES PATENTS

| 2,897,119 | 7/1959 | Dunn ................................. | 424/344 |
| 3,070,499 | 12/1962 | Mullins et al. ..................... | 424/344 |
| 3,708,583 | 1/1973 | Winstrom et al. ................. | 424/344 |

FOREIGN PATENTS OR APPLICATIONS

| 748,221 | 4/1956 | United Kingdom ............... | 424/344 |

*Primary Examiner*—Norman A. Drezin
*Attorney, Agent, or Firm*—Samuel L. Welt; Bernard S. Leon; William M. Farley

[57] ABSTRACT

High potency compositions of vitamin A acetate and/or vitamin A alcohol stabilized against the formation of crystals by vitamin A palmitate are provided.

6 Claims, No Drawings

HIGH POTENCY VITAMIN A COMPOSITIONS

RELATED APPLICATIONS

This is a continuation, of application Ser. No. 397,192 filed Sept. 13, 1973, and now abandoned which is, in turn, a continuation of application Ser. No. 111,120, filed Jan. 11, 1971 and now abandoned, which is, in turn, a continuation-in-part of application Ser. No. 816,106, filed Apr. 14, 1969 and now abandoned.

BACKGROUND OF THE INVENTION

In recent years there has been a considerable amount of research directed to the formulation of vitamin preparations of very high potency, particularly solutions or liquids. Such high potency vitamin products may be utilized as injectable preparations, particularly in veterinary medicine, or as concentrated vitamin preparations by the pharmaceutical, food and related industries. It has been recognized that vitamin A acetate is a desirable form of vitamin A for the preparation of such injectables and liquid vitamin concentrates as it is a high potency source of vitamin A and it is less expensive than other common esters of vitamin A such as the palmitate. Vitamin A alcohol is also desirable for such preparations as it is the most potent source of vitamin A activity in terms of U.S.P. units per milligram.

The major problem inherent in the use of vitamin A acetate and vitamin A alcohol in high potency vitamin preparations is that they have a low solubility in most of the lipophilic solvent systems used to prepare high potency vitamin products of the fat soluble vitamins, e.g., vitamins A, D and E. In such preparations there is a strong tendency for vitamin A acetate and alcohol to separate from such preparations as crystals. The problem of crystallization is most pronounced with multiple vitamin preparations wherein the concentration requirements of the final product and the presence of other vitamins, preservatives and the like do not allow for the incorporation of sufficient excipients to prevent the formation of crystals of vitamin A acetate.

For example, vitamin A preparations containing 1 million units of vitamin A activity per ml. are known in the art utilizing vitamin A palmitate. For the preparation of injectable solutions with good biological mobility utilizing other vitamins, preservatives, emulsifiers and other additives, however, the use of the palmitate does not allow sufficient room in the preparation for proper quantities of these other ingredients. Vitamin A acetate, which can be incorporated into such a preparation with sufficient room for these other ingredients, unfortunately often forms crystals within a short time after the preparation is prepared. Vitamin A alcohol exhibits similar characteristics. It is manifest that a relatively low cost, ultrahigh potency vitamin A formulation utilizing the more potent vitamin A acetate would be possible if it were possible to prevent the vitamin A acetate from crystallizing out of the final preparation. It is an object of the instant invention to provide such a vitamin A preparation.

BRIEF SUMMARY OF THE DISCLOSURE

The instant invention is predicated on my discovery that the addition of vitamin A palmitate to preparations containing high concentrations of vitamin A acetate or vitamin A alcohol will stabilize such preparations against the formation of crystals of acetate or alcohol.

DETAILED DESCRIPTION OF THE INVENTION

The vitamin A preparations of the instant invention contain at least about 40 percent by weight of vitamin A palmitate calculated on the weight of the vitamin A acetate or vitamin A alcohol present. Preferred compositions contain from about 40 percent to about 100 percent by weight vitamin A palmitate based on the weight of either vitamin A acetate or alcohol present. These preparations contain a high potency of vitamin A activity, yet remain fluid and non-crystalline in the lipophilic solvent systems used to prepare such preparations over a wide range of practical temperatures.

The compositions of the present invention may be formulated in a wide variety of strengths and forms. Most important, form a practical viewpoint, the compositions of the present invention can be formulated into stable preparations containing 1 million units of U.S.P. vitamin A activity or more which are free from crystal formation. These preparations may contain only vitamin A, or they may contain additional vitamins, additives, preservatives and the like.

The foregoing is not intended to indicate that preparations containing a million or more U.S.P. units of vitamin A activity per ml. are unknown in the art. Such preparations containing vitamin A palmitate are well known in the art. Palmitate, as has been stated, is unsatisfactory for injectable multiple vitamin preparations as the room physically taken up by the presence of the palmitate does not leave sufficient room for the addition of the other vitamins, emulsifiers, preservatives and the like. Similar preparations utilizing vitamin A acetate have sufficient room for the additional ingredients, but possess the disadvantage of the vitamin A acetate crystallizing out of the solution in the finished preparation. My discovery that the presence of from about 40 percent by weight, more preferably 40 to 100 percent by weight, of vitamin A palmitate based on the weight of vitamin A acetate will prevent the latter from crystallizing from solution not only allows the less expensive, more potent acetate to be utilized in such high potency preparations but makes possible the incorporation of other vitamins, additives, preservatives and the like in stable preparations containing a million or more U.S.P. units of vitamin A activity. The inclusion of the vitamin A acetate in preparations such as herein described also, on the average, reduces the cost of the finished product to the consumer over that of a similar preparation containing all palmitate. The cost of the palmitate-acetate combination may well be less in the total evaluation as the user would, in all probability, discard and replace pure acetate preparations where crystal formation and growth had occurred. The presence of such crystals is particularly undesirable in injectable preparations.

The compositions according to the present invention may be formulated into a wide variety of preparations. Such preparations would include injectable solutions, water-dispersible concentrates, liquid feed supplements, vitamin-containing liquids for oral administration, concentrates designed for vitamin enrichment of such products as margarine or milk and the like.

It has been found that commercial preparations of the above types could be formulated utilizing the compositions of the present invention at a cost savings of from 15 to 25 percent or higher over similar preparations presently known in the art. This reduction in cost represents reductions in inert diluents, non-vitamin A materials, packaging, handling and the like made possible by the formulation of stable, concentrated, high-potency vitamin A preparations utilizing the compositions of the present invention. A cost reduction has been found even over prior art vitamin A acetate preparations, as such preparations utilize various substances which do not have vitamin A activity in an attempt to stabilize the vitamin A acetate against crystallization. The compositions of the present invention, on the other hand, use less vitamin A acetate and achieve a more concentrated, more potent preparation by stabilizing the vitamin A acetate with vitamin A palmitate.

The vitamin A compositions according to the present invention may be incorporated into anhydrous, water-dispersible preparations, lipophilic vehicles and aqueous dispersions.

The vitamin-active oil preparations as contemplated herein may include in addition to the vitamin A compositions of the present invention, other fat-soluble vitamin-active compounds such as vitamin $D_2$, vitamin $D_3$, vitamin E and the like.

The identity of the lipophilic solvents contemplated herein is not critical as long as they are pharmaceutically acceptable and non-toxic. They may include, for example, any generally used animal or vegetable oil suitable for the formulation of injectables. In the anhydrous water-dispersible preparations or emulsions intended for oral administrtion to humans or animals, edible triglyceride oils, particularly coconut oil or a vegetable oil such as, for example, cottonseed oil, corn oil or the like are generally utilized.

Where the compositions of the present invention are to be formulated into emulsions or water-dispersible concentrates, a number of emulsifying agents may be included therewith. The identity of these emulsifying agents is not critical as long as they are pharmaceutically acceptable, non-toxic and compatible with the ingredients in the injectable solutions. Representative of such emulsifying agents are the polyoxyethylene ethers of castor oil which are marketed under various tradenames such as the Creamaphor, Emulphor, Prosol E and Lipal compounds. Other emulsifying agents which may be utilized herein include the commercially available polyoxyethylene sorbitan monostearates and the like. Of course, as the choice of a suitable emulsifying agent is well within the purview of a person skilled in the art, the foregoing examples are not intended in any way as being limiting on the scope of the present invention.

In addition to the ingredients enumerated heretofore, the compositions of the present invention can contain preservatives, antioxidants and other adjuvants and excipients which are customarily utilized in the types of preparations enumerated herein. The identity of the preservative or antioxidant is not critical as long as they are pharmaceutically acceptable, non-toxic and compatible with the ingredients in the injectable solution. In general, any conventional preservative or any conventional antioxidant meeting the above criteria may be utilized in the formulation of products containing the compositions of the instant invention. As a preservative the following recognized preservatives are exemplary: sodium ethylmercurithiosalicylate, benzyl alcohol, chlorobenzyl alcohol, dichlorobenzyl alcohol, chlorobutanol, phenol, methyl-p-hydroxybenzoate, propyl-p-hydroxybenzoate and the like.

As an antioxidant, the following recognized antioxidants are exemplary: butylated hydroxyanisole, butylated hydroxytolouene, propyl gallate, EMQ (6-ethoxy-1,2-dihydro-2,2,4-trimethylquinoline), α-tocopherol, ascorbic acid, ascorbyl palmitate, alkali metal salts of ascorbic acid and the like. Mixtures of antioxidants may be used if desired. While an antioxidant is an optional ingredient of the products of this invention, it is preferred to incorporate an antioxidant or a mixture of antioxidants into the compositions of the instant invention. A preferred antioxidant mixture is equal parts by weight of butylated hydroxyanisole and butylated hydroxytoluene to a total weight which comprises up to about 0.3 percent by weight of the final product, or a total of from 5 to 50 mg. per million U.S.P. units of vitamin A activity. Another preferred antioxidant is EMQ, used at a level of from about 50 to about 300 mg. per million U.S.P. units of vitamin A activity.

Other diluents, excipients and the like which may be included in preparations formulated utilizing the compositions of the instant invention are believed to be completely within the purview of the skilled technician and will not be enumerated herein.

As has been heretofore indicated, the stable vitamin A compositions of the present invention contain at least about 40, preferably from about 40 to about 100 percent, vitamin A palmitate based on the weight of the vitamin A acetate or vitamin A alcohol present in the final preparation. The exact proportions of vitamin A palmitate to vitamin A acetate or vitamin A alcohol necessary to form a preparation stable against the formation of crystals will depend on such factors as the concentration of the vitamin A fraction in the finished product, the vehicle composition and the like. Generally, however, a minimum of about 30 percent by weight vitamin A palmitate calculated on the weight of the vitamin A acetate or vitamin A alcohol is required to form a stable preparation. As has been stated, the preferred range of vitamin A palmitate based on the weight of vitamin A acetate or vitamin A alcohol is between about 40 and about 80 percent. This preferred range of vitamin A palmitate will stabilize vitamin A acetate or vitamin A alcohol in nearly all of the commercial preparations contemplated herein. In any event, a concentration of vitamin A palmitate greater than that of either vitamin A acetate or vitamin A alcohol is usually neither required nor desired as contemplated herein. The exact proportions of the vitamin A palmitate, vitamin A acetate or vitamin A alcohol within the stated ranges may be easily determined for a particular type of preparation with a certain potency by the skilled artisan. Specific examples of preparations prepared utilizing the compositions of the present invention may be found in the appended preparations and examples.

The following table, Table 1, illustrates the effect of vitamin A palmitate on vitamin A acetate at room temperature (about 25° C.) at different concentrations after storage for 1 year. The vitamin A palmitate is reported as percent by weight based on the weight of the vitamin A acetate present.

Table I

| Preparation No. | Palmitate % | Appearance |
| --- | --- | --- |
| 1 | — | Solid |
| 2 | 43 | Liquid-some crystals |
| 3 | 67 | Clear Liquid |
| 4 | 100 | Clear Liquid |
| 5 | 150 | Clear Liquid |

Table I-continued

| Preparation No. | Palmitate % | Appearance |
|---|---|---|
| 6 | 233 | Clear Liquid |

After storage for one year at 5° C., preparation 2 above showed only a very small amount of crystals while preparations 3 to 6 were clear. This observation is significant in that both vitamin A acetate and vitamin A palmitate in the pure state are solids at 5° C.

The above preparations were seeded with crystals of vitamin A acetate in an attempt to force crystallization. No apparent change was observed in any of the preparations.

In Table II a comparison is made between vitamin A acetate alone and in the presence of vitamin A palmitate both at room temperature and at normal refrigeration temperature of 5° C. The comparisons were made in a series of preparations utilizing various solvents and, in several instances, additional vitamins. All samples showing no crystal growth were seeded to induce growth. No change was noted.

Table II

| Vitamin A Potency* U.S.P.U/gm | Vitamin A Acetate mg/gm | Vitamin A Palmitate mg/gm | Vitamin E Acetate mg/gm | Vitamin $D_3$ Resin mg/gm | Solvent or diluent mg/gm | Crystal Growth 5° C. | Crystal Growth Room Temp. |
|---|---|---|---|---|---|---|---|
| 400,000 | 110 | 110 | 240 | 5 | EMQ[1] (60) Tween 60[20] (400) 95 percent Ethyl Alc (75) | neg | neg |
| 400,000 | 110 | 110 | | 5 | EMQ (60) Tween 60 (400) 95 percent Ethyl Alc (75) Neobee M-5[3] (240) | neg | neg |
| 400,000 | 110 | 110 | | 5 | EMQ (60) Tween 60 (400) 95 percent Ethyl Alc (75) Drewplast 030[3] (120) Corn Oil (120) | neg | neg |
| 400,000 | 110 | 110 | | 5 | EMQ (60) Tween 60 (400) 95 percent Ethyl Alc (75) Drewplast 030 (120) Neobee M-5 (120) | neg | neg |
| 400,000 | 110 | 110 | | 5 | EMQ (60) Tween 60 (400) 95 percent Ethyl Alc (75) Glycerol monooleate (240) | neg | neg |
| 400,000 | 110 | 110 | 240 | 6 | EMQ (35) Tween 60 (400) 95 percent Ethyl Alc (50) Propylene glycol (49) | neg | neg |
| 400,000 | 110 | 110 | | 6 | EMQ (35) Tween 60 (400) 95 percent Ethyl Alc (50) Propylene glycol (50) | neg | neg |
| 500,000 | 220 | | | | EMQ (50) Tween 60 (350) 95 percent Ethyl Alc (50) Propylene glycol (30) Corn Oil (300) | pos | pos |
| 500,000 | 220 | | | | EMQ (50) Tween 60 (350) 95 percent Ethyl Alc (50) Propylene glycol (30) Decaglycerol Octa-oleate (330) | pos | pos |
| 500,000 | 220 | | 300 | | EMQ (50) Tween 60 (350) 95 percent Ethyl Alc (50) Propylene glycol (30) | pos | pos |
| 500,000 | 220 | | | | EMQ (50) 95 percent Ethyl Alc (350) Tween 60 (350) Propylene glycol (30) | pos | pos |
| 500,000 | 220 | | | | EMQ (50) 95 percent Ethyl Alc (200) Propylene glycol (180) | pos | pos |

Table II-continued

| Vitamin A Potency* U.S.P.U/gm | Vitamin A Acetate mg/gm | Vitamin A Palmitate mg/gm | Vitamin E Acetate mg/gm | Vitamin D$_3$ Resin mg/gm | Solvent or diluent mg/gm | Crystal Growth 5° C. | Crystal Growth Room Temp. |
|---|---|---|---|---|---|---|---|
| 500,000 | 220 | | | | Tween 60 (350) EMQ (50) | pos | pos |
| 500,000 | 220 | | | | Tween 60 (500) 95 percent Ethyl Alc (200) Propylene glycol (30) EMQ (50) Glycerol trioleate (300) Tween 60 (350) 95 percent Ethyl. Alc (50) Propylene glycol (30) | pos | pos |

*Approximate potency with normal manufacturing excess common to the trade.
¹EMQ is an abbreviation for 6-ethoxy-1,2-dihydro-2,2,4-trimethylquinoline (Ethoxyquin).
²Tween 60 is a trademark for a polyoxyethylene derivative of sorbitan monostearate.
³Neobee M-5 and Drewplast 030 are coconut oil fractions; Drewplast 030 is a partially hydrolyzed fraction marketed by the Drew Chemical Co., Boonton, New Jersey.

To further illustrate the stability of the compositions of the present invention the following vitamin A preparations for injection containing one million units of vitamin A activity for injection were prepared.

PREPARATIONS A AND B

| Ingredient | Formulation mg/cc A | Formulation mg/cc B |
|---|---|---|
| Vitamin A acetate | 338 | 338 |
| Vitamin A palmitate | 140 | 140 |
| Vitamin E acetate | 112 | 112 |
| Ethyl alcohol, anhydrous | 0.10 cc | 0.15 cc |
| BHA¹ | 10 | 10 |
| BHT² | 10 | 10 |
| Benzyl Alcohol | 0.02 cc | 0.02 cc |
| Emulphor EL-620³ q.s. | 1 cc | 1 cc |

¹Butylated hydroxyanisole
²Butylated hydroxytoluene
³Trademark for a polyoxyethylene ether of castor oil Samples of Preparations A and B were seeded with crystals of vitamin A acetate. After 2 months storage at 5° C., both preparations were clear. Both preparations remained clear after 6 months storage at room temperature.

PREPARATION C

Preparation C was formulated exactly as Preparations A and B only utilizing 432 mg. of vitamin A acetate and no vitamin A palmitate. This preparation exhibited crystals of vitamin A acetate both at room temperature and 5° C. within a few hours after preparation. This preparation was not seeded to induce crystallization.

PREPARATION D

| Ingredient | Formulation mg/cc |
|---|---|
| Vitamin A acetate | 338 |
| Vitamin A palmitate | 140 |
| Vitamin E acetate | 112 |
| BHA | 10 |
| BHT | 10 |
| Vitamin D$_2$ | 6 |
| Ethyl alcohol, anhydrous | 0.1 cc |
| Benzyl Alcohol | 0.02 cc |
| Emulphor EL-620 q.s. | 1.0 cc |

Samples of Preparation D were seeded with vitamin A acetate and stored at 5° C. After 2 months storage there was no crystal growth. Similar preparations which were not seeded before storage under the same conditions remained clear. Both seeded and unseeded samples stored at room temperature for 6 months showed no crystal growth.

PREPARATION E

| Ingredient | Formualation mg/cc |
|---|---|
| Vitamin A alcohol | 250 mg. |
| Vitamin A palmitate | 250 mg. |
| Vitamin E acetate | 120 mg. |
| Tween 80 | 40 mg. |
| Benzyl alcohol | 0.02 cc |
| BHA | 7.5 |
| BHT | 7.5 |
| Ethyl alcohol, anhydrous | 0.1 cc |
| Modified coconut oil fraction, q.d. | 1.0 cc |

Samples of this preparation were stored at room temperature and at 5° C. for 6 months. All samples were clear after 6 months.

The preparations as formulated utilizing the compositions of the present invention are useful in supplying the vitamin requirements of man as well as domestic animals and fowl by direct oral or parenteral administration or by the fortification of various foods and feedstuffs. The compositions of the instant invention have been found to be both completely stable and completely biologically active when used in preparations suitable for the aforementioned methods of administering vitamins. The precise manner in which the present compositions are used and the dosage levels to be employed will be immediately apparent to persons skilled in the art.

For a fuller understanding of the nature and objects of this invention reference may be had to the following examples which are given merely as an illustration and are not to be construed in a limiting sense.

EXAMPLE 1

An anhydrous water-dispersible vitamin concentrate was formulated in the following manner, all parts being given in mg. per gram:

110 Mg. vitamin A acetate was heated to between 45° and 50° C. to liquify for handling. 110 Mg. vitamin A palmitate was added to the acetate, maintaining a temperature of about 45° C. in a jacketed kettle. 400 Mg. Tween 60 was warmed to 45° C. to liquify. A small portion was separated and 5 mg. vitamin D$_3$ was dissolved therein. This portion and the remaining Tween 60 were then added to the vitamin A component. To this mixture was added 60 mg. ethoxyquin (EMQ) and 230 mg. vitamin E acetate (dl-α-tocopherylacetate). 10 Mg. of selected edible coconut oil fractions, which are mostly triglycerides of medium chain fatty acids, were warmed to about 45° C. and added to the mixture. The whole was then cooled below 30° C., with stirring, and 75 mg. of 95 percent ethyl alcohol was added. Stirring was continued for about 30 minutes and the preparation was filtered to yield a clear dark solution. The solution thus formed will disperse in water to form a stable, opalescent emulsion of very fine particles of the vitamin.

These liquid preparations may be utilized to form oral liquid vitamin preparations or in the fortification or foodstuffs. For agricultural purposes, the liquids may be added to vehicles such as molasses to form stable liquid feed supplements.

EXAMPLE 2

A stable, injectable preparation with a potency of one million U.S.P. units of vitamin A activity was formulated as follows, all quantities being given in mg. per ml.:

10 Mg. of butylated hydroxytoluene, 10 mg. of butylated hydroxyanisole and 6 mg. of vitamin $D_2$ were added to and heated to a temperature of about 85° C. in 100 mg. of Emulphor EL-620. 338 Mg. of vitamin A acetate were heated to about 50° C. and 140 mg. of vitamin A palmitate were added thereto. 112 Mg. of vitamin E acetate (dl-α-tocopherylacetate) and 0.2 ml. of benzyl alcohol were added to the vitamin A component and it was then combined with the Emulphor EL-620 and the whole was cooled to about 30° C. with stirring. 0.15 Ml. anhydrous ethyl alcohol was added to the preparation and the volume was adjusted to 1.0 ml. with Emulphor EL-620. There was obtained by this procedure a vitamin A, $D_2$ and E preparation suitable for administration to animals and poultry by parenteral means. When administered parenterally, the product was completely biologically available and did not cause significant tissue irritation.

I claim:

1. A vitamin A active solution, containing from about 400,000 to about 1 million units of vitamin A per gram of solution, stable against crystallization of vitamin A comprising:
   a. a vitamin A active material consisting of
      i. a vitamin A compound selected from the group consisting of vitamin A acetate and vitamin A alcohol together with
      ii. from about 40 percent to about 100 percent by weight based on the weight of (i) of vitamin A palmitate and
   b. a pharmaceutically acceptable lipophilic solvent selected from the group consisting of animal oil and vegetable oil.

2. The stable vitamin A active solution according to claim 1 wherein (a) (i) is vitamin A acetate.

3. The stable vitamin A active solution according to claim 1 wherein (a) (i) is vitamin A alcohol.

4. The stable vitamin A active solution according to claim 1 wherein there is also present a non-toxic pharmaceutically acceptable preserving agent.

5. The stable vitamin A active solution according to claim 1 wherein there is also present a non-toxic pharmaceutically acceptable anti-oxidant.

6. A vitamin A active solution stable against crystallization of vitamin A consisting essentially of a solution of vitamin A acetate in vitamin A palmitate wherein the vitamin A palmitate content ranges from about 67 percent to 233 percent by weight, based on the weight of the vitamin A acetate.

* * * * *